United States Patent [19]
Frankenfeld et al.

[11] 3,970,759
[45] July 20, 1976

[54] ALIPHATIC DIOLS AS PRESERVATIVES FOR COSMETICS AND RELATED PRODUCTS

[75] Inventors: John W. Frankenfeld, Atlantic Highlands, N.J.; Donald L. Wright, New York, N.Y.

[73] Assignee: Exxon Research and Engineering Company, Linden, N.J.

[22] Filed: Aug. 19, 1974

[21] Appl. No.: 498,651

Related U.S. Application Data

[63] Continuation of Ser. No. 313,781, Dec. 11, 1972, abandoned, which is a continuation-in-part of Ser. No. 67,270, Aug. 26, 1970, abandoned.

[52] U.S. Cl. ............................... 424/343; 424/63; 424/69; 424/70; 424/311; 424/312; 424/313

[51] Int. Cl.$^2$ ........................................... A01N 9/24
[58] Field of Search ................................... 424/343

[56] References Cited
UNITED STATES PATENTS
2,446,505   8/1948   Arenson ............................ 424/311

OTHER PUBLICATIONS
Chemical Abstracts, vol. 75, (1971), p. 87713e.

*Primary Examiner*—V. D. Turner
*Attorney, Agent, or Firm*—Joseph J. Dvorak

[57] ABSTRACT

Cosmetics and personal care products are protected from spoilage due to microbial attack by the addition of certain poly alcohols and their esters, such as 1,3-diols and the mono- or diesters of such diols.

5 Claims, No Drawings

ALIPHATIC DIOLS AS PRESERVATIVES FOR COSMETICS AND RELATED PRODUCTS

CROSS-REFERENCES

This is a continuation of application Ser. No. 313,781, filed Dec. 11, 1972, and now abandoned, which in turn is a continuation-in-part of application Ser. No. 67,270 filed Aug. 26, 1970, also now abandoned.

FIELD OF INVENTION

The present invention is concerned generally with the use of particular diols and their esters as preservatives in various preparations subject to microbial attack and deterioration such as personal care preparations, cosmetic preparations and the like. The additives of the present invention are particularly desirable since they are effective in inhibiting and/or controlling the growth of microorganisms typically found in such preparations thereby increasing the shelf life of the preparations. They have very desirable physical properties for combining them in cosmetics, personal care products and the like. Most importantly, these preservatives are not toxic to humans.

BACKGROUND OF INVENTION

There is a wide variety of materials employed in personal care and cosmetic preparations that is subject to microbial attack and concomitant deterioration. For example, oils such as cocoanut oil, sesame oil, peanut oil and the like, are frequently used in cosmetic and personal care preparations as vehicles, carriers and emollients. Mold spores and similar organisms are known to be able to thrive on such oils. The net effect is ultimate deterioration of preparations containing such oil vehicles. The result is not only an economic loss but often the user is unsuspectingly and unnecessarily exposed to potentially harmful organisms.

Other materials are also susceptible to microbial attack. For example, organic nitrogen compounds such as nitrogeneous surfactants, proteins, protein hydrolysates, and the like used in popular cosmetics and shampoos are utilized by a wide variety of microorganisms thereby shortening the shelf-life of preparations incorporating these materials.

Thus, there is a need for protecting or preserving preparations subject to microbial attack against the growth of these harmful microorganisms so as to extend the shelf-life and improve the quality of the preparations.

It should be noted that even if cosmetics and personal care preparations are formulated under the most carefully controlled conditions designed to minimize microbial contamination, ultimately the container is opened by the user and thereby brought into contact with air borne organisms or organisms carried by the user. Thus, control of manufacturing conditions is not sufficient in itself to assure desirable resistance of the preparation to microbial deterioration.

Preservation of cosmetics and personal care products by use of additives is not a simple task. Many materials, for example, are known germicides or bactericides. Unfortunately, few highly effective antimicrobials are sufficiently safe for use in contact with humans. Additionally, any preservative employed must be easily combinable with typical cosmetic and personal care preparations without detrimentally affecting the overall physical properties of such preparations.

SUMMARY OF THE INVENTION

According to the present invention, there is provided a method of inhibiting the growth of microorganisms in cosmetic and personal care compositions normally capable of supporting microbial growth, by incorporating in the compositions an effective amount of a preservative selected from the group consisting of linear aliphatic 1,3-diols having 5 to 15 carbon atoms in the molecule, mono- and diesters of said 1,3-diols, said esters having linear aliphatic acyl groups of from 2 to 20 carbon atoms, whereby the composition is preserved against microbial deterioration. As used herein, the term "cosmetic" is intended to include preparations which are used to improve the tone, color, general health and appearance of the skin. The term "personal care" preparations as used herein includes compositions which are used to promote cleanliness. Face make-up and creams are examples of the former, while shampoos are an example of the latter. Thus, in one sense, the present invention is concerned with preserving cosmetics and personal care compositions containing microbial degradable substances against deterioration so as to improve the shelf and use life of these compositions.

In a preferred embodiment of the present invention, emollient compositions containing oils, especially edible oils, are preserved against microbial deterioration by incorporating in the compositions an effective amount of a preservative selected from linear aliphatic 1,3-diols, mono- and diesters thereof, said diols having 5 to 15 carbon atoms in the chain and said esters having a linear aliphatic acyl group of 2 to 20 carbon atoms.

In yet another preferred embodiment of the present invention there is provided a method of preserving compositions containing organic nitrogen compounds such as protein-containing cosmetics, shampoos and the like, against microbial decay by incorporating the above mentioned specific 1,3-diols and the mono- and diesters of the diols in such compositions.

These and other features of the present invention will be better understood from the detailed description which follows.

DETAILED DESCRIPTION

As previously indicated the present invention is based, in part, on the discovery that particular linear aliphatic diols and their esters can be used as additives in compositions normally subject to microbial deterioration, such as cosmetic and personal care products, especially those containing oils and organic nitrogen compounds. Incorporation of these additives in these compositions will protect them against various public health implicated bacteria, yeasts and molds. These aliphatic diols, such as aliphatic 1,3-diols of 5 carbon atoms or more are nontoxic compounds which are very excellent when utilized for the production of high quality products which come into contact with the human body. These compounds have advantages over current additives not only because of increased effectiveness, but also because they are very safe to use.

These additive materials are easily synthesized and have very desirable physical properties. The diols are colorless, virtually odorless and tasteless and are readily formulated into various cosmetic and personal care products. Since they are produced by chemical means from readily obtainable starting materials, they have advantages in that they are available at stable prices and in consistent quantities.

These linear aliphatic polyols contain from about 5 to 15 carbon atoms in the molecule, preferably about 7 to about 10 carbon atoms in the molecule. The polyols of the present invention contain hydroxy groups on at least the first and third carbon atoms of the molecule. It is this 1,3-dihydroxy configuration which renders these compounds very useful as additives because of their inherent safety. Poly alcohols with hydroxyl groups in other positions on the carbon chain are toxic and, therefore, are not useful additives. In addition to being nontoxic, the 1,3-diols claimed herein have certain other advantages making them highly desirable as cosmetic and personal care product additives: (1) they are stable, nonvolatile oils or low melting solids and have a long storage and shelf life; (2) they have an appreciable water solubility and/or are readily emulsified, making them easy to formulate in compositions intended for use in cosmetics and shampoos.

As indicated, the mono- and diesters of the 1,3-diols of 5 to 15 carbon atoms are also useful as preservatives for cosmetic and personal care products. The esters of these 1,3-diols have linear aliphatic acyl groups of from 2 to about 20 carbon atoms.

A summary of the compounds specifically claimed in this invention, along with their physical properties, is presented in Table I.

TABLE I

| Diol | BP/mm (°C.) | Taste, Odor, etc. |
|---|---|---|
| 1,3-pentanediol | 78–81/0.5 | Colorless, sweet odor, bitter taste |
| 1,3-hexanediol | 81–82/0.2 | Colorless, slight musty odor, bitter taste |
| 1,3-heptanediol | 90/0.5 | Colorless, slight musty odor, slight bitter taste |
| 1,3-octanediol | 87–89/0.3 | Colorless, slight musty odor, slight bitter taste |
| 1,3-nonanediol | 126/1.1 | Colorless, slight musty odor, slight bitter taste |
| 1,3-decanediol | mp[1]=30–31 | Colorless, slight musty odor, slight bitter taste |
| 1,3-undecanediol | mp[1]=41–42 | Colorless, slight musty odor, slight bitter taste |

[1]mp = melting point.

This invention is not limited to these specific compounds. Any 1,3-diol containing more than 5 carbons or its mono- or diester may prove useful for one or more applications as a preservative for cosmetics and personal care products. Particularly desirable additives are:

1,3-Heptanediol
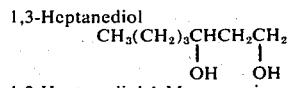
Formula: $C_7H_{16}O_2$ 1,3-Heptanediol-1-Monopropionate
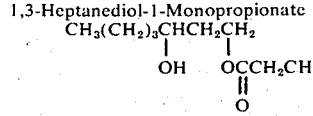
Formula: $C_{10}H_{20}O_3$ 1,3-Heptanediol dipropionate
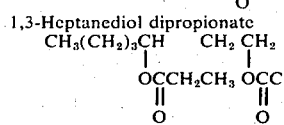
Formula: $C_{13}H_{24}O_4$ -continued 1,3-Octanediol-1-Monopropionate
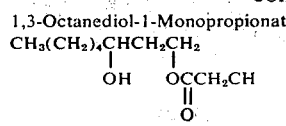
Formula: $C_{11}H_{22}O_3$ While the diols may be prepared by any satisfactory method, the following methods are very satisfactory for their preparation.

The Reformatsky reaction followed by reduction:

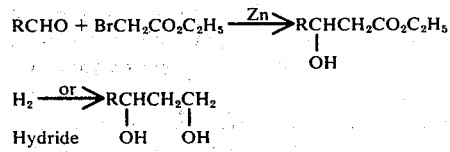

or by means of the Prins reaction of formaldehyde and the appropriate α olefin or mixtures of α olefins:

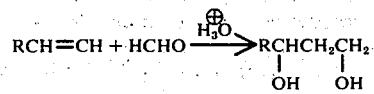

The esters of aliphatic 1,3-diols are synthesized easily. These materials are colorless, odorless and tasteless, and are easily formulated into cosmetic and personal care products. In addition, they possess a unique ability to preserve these products against microbial deterioration. Since they are produced by chemical means from readily obtainable starting materials, the esters of 1,3-diols have marked advantages in that they are available at stable prices and in consistent quantities.

The esters are made from diols by reacting them with linear aliphatic fatty acids or fatty acid derivatives which contain from about 2 to 20 carbon atoms in the molecule, preferably 3 to 18 carbon atoms, such as about 8 carbon atoms in the molecule. In general, the esters have the following configuration:

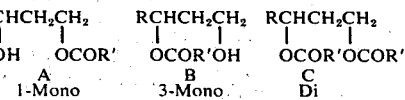

where R represents a straight chain alkyl group containing from 1 to 12 carbons and R' represents the alkyl portion of an aliphatic carboxylic acid containing 2 to 20 carbon atoms. The compounds may be varied in molecular weight as long as the 1,3-configuration is preserved. These esters are conveniently prepared either from the diols by reaction with the appropriate acid, acid anhydride or acid chloride:

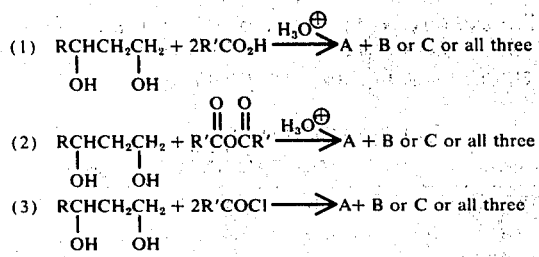

or, in the case of the diester, C, by means of the Prins reaction of formaldehyde and an α olefin in the presence of the desired acid:

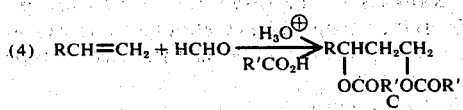

The best materials are those with 5 to 8 carbon hydrocarbon "tail" in either the diol or ester portion of the compound combined with a concentration of polar groups in another part of the molecule, as, for example, 1,3-octanediol-1-mono-propionate. Some especially valuable esters are shown in the following Table II.

TABLE II

| PROPERTIES OF SOME 1,3-DIOL ESTERS | |
|---|---|
| Compound | BP°C. (mm) |
| 1,3-Hexanediol | — |
| 1-monoacetate | 59–62 (0.15) |
| 1-monooctanoate | 117–122 (0.3) |
| 1-monopalmitate | 124–126 (0.2) |
| diacetate | 81–82 (0.9) |
| 1,3-Heptanediol | |
| 1-monooctanoate | 85–90 (1.0) |
| 1-monopalmitate | MP* =38–39 |
| dipropionate | 90–92 (0.4) |
| 1,3-Octanediol | |
| 1-monopropionate | 83–86 (0.3) |

*MP = melting point

In order to further illustrate the invention, various tests were carried out, the results of which are described in the following examples and tables of data. In Table III are summarized the results of toxicity measurements. These studies were conducted with rats.

TABLE III

| TOXICITY DATA FOR VARIOUS DIOLS | | |
|---|---|---|
| Compounds | Polyols | Oral $LD_{50}$ (7 days)[1,2] |
| 1 | 1,3-Pentanediol | >20 g/kg |
| 2 | 1,5-Pentanediol | 2 g/kg |
| 3 | 1,3-Hexanediol | >20 g/kg |
| 4 | 1,5-Hexanediol | >20 g/kg |
| 5 | 2,5-Hexanediol | 2 g/kg |
| 6 | 1,6-Hexanediol | 5 g/kg |
| 7 | 1,3-Heptanediol | >20 g/kg |
| 8 | 1,3-Octanediol | >20 g/kg |
| 9 | 1,3-Nonanediol | >20 g/kg |
| 10 | 1,3-Decanediol | >20 g/kg |
| 11 | 1,3-Undecanediol | >20 g/kg |

[1]Single dose rats.
[2]$LD_{50}$ = lethal dose for 50% kill.

It is apparent from the above data that the positioning of the hydroxyl groups has a very significant effect on the toxicity of these compounds. Having hydroxyl groups on the first and third carbon atoms of the chain is sufficient to reduce the toxicity and render the compounds completely safe for products to be used in contact with the human body and to be stored with complete safety. Thus, there exists no danger of these products causing harm by accidental use either by adults or by children.

$LD_{50}$ values are a common measure of the toxicity of a compound. These $LD_{50}$ values represent the lethal dose for a 50% kill of the animals tested per unit weight of the animals. The higher the $LD_{50}$ value, the lower the toxicity. The data in Table III establish that the 1,3-configurations of poly alcohols are the least toxic. The $LD_{50}$ values are significantly higher in compounds possessing this structural feature. The $LD_{50}$ values given in Table III were obtained by giving test animals graded single doses of the test compounds orally and observing them for one week. The number of deaths in each group was noted and the dose required for a 50% kill taken as the $LD_{50}$ value. In many cases, no death occurred even at the 20 g/kg level (about as much as one can give a rat in one dose), hence the basis of the "20" values shown in the table.

The toxicity data with respect to the esters of 1,3-diols are given in the following Table IV. The $LD_{50}$ values for some common preservatives are also shown. All are significantly more toxic (lower $LD_{50}$ values) than either the diols or the esters.

TABLE IV

| TOXICITY DATA | |
|---|---|
| Preservative | Oral $LD_{50}$ (Rats)[1] |
| 1,3-Diol Esters ($C_5$ and higher) | >20 g/Kg |
| Sorbic Acid[2] | 10 g/Kg |
| Sodium Sorbate[2] | 6–7 g/Kg |
| Propionic Acid[3] | 4 g/Kg |
| Sodium Benzoate[2] | 2–3 g/Kg |

[1]$LD_{50}$ = lethal dose for 50% kill.
[2]Source: Handbook of Toxicology, Vol. I, W. S. Spector ed., WADC Tech. Rept. No. 55-16, National Academy of Sciences, National Research Council (1955).
[3]Source: H. F. Smyth et al., Am. Ind. Hyg. Assoc. J., 23, 95 (1962).

In addition to being nontoxic the preservatives of this invention have been tested for skin irritancy by the method of Klegman and Wooding, *J. Invest. Derm.*, vol. 49, 78–94 (1967) and judged to be very unlikely to cause irritation in normal subjects under normal conditions of use.

The diols and their esters may be incorporated into cosmetic and personal care products in any way in accordance with law. The compounds are added in effective amounts generally ranging from .05% to about 5.0% by weight based on the total weight of the composition. Preferably, from about 2.0% to about 5.0% by weight of the preservative is used. The diols and diol esters of the present invention are particularly effective in preserving cosmetic and personal care products against microbial deterioration, especially cosmetic and personal care products containing oil vehicles and emollients and organic nitrogen compounds. For example, cosmetics containing oils, such as edible oils including peanut oil, safflower oil, sesame oil and whale oil and containing emollients, such as hydrocarbon greases including petrolatum, lanolin and spermaceti can be preserved against microbial contamination in accordance with the present invention. Similarly, personal care products containing organic nitrogen compounds including alkylolamides, proteins, protein hydrolysates and amino acids can be preserved in accordance with the present invention.

A very suitable shampoo, for example, comprises the following:

| Ingredient | % by Weight | % by Weight Range |
|---|---|---|
| Duponol WAT[a] | 52.00 | 30–70 |
| Monamid LMWC[b] | 10.00 | 5–11 |
| Diol or Diol Ester[c] | 0.20 | 0.01–1.0 |
| Water | 37.43 | 10.0–50.0 |
| Perfume | 0.25 | 0.01–1.0 |

[a] See Zimmerman and Lavine Trade Names, 1953 edition, page 189.
[b] See Zimmerman and Lavine Trade Names, Supplement 1, page 147.
[c] Any of compounds listed in Tables I, II, or III, i.e., 1,3-Heptanediol.

A very desirable vanishing cream produced in accordance with the present invention is of the following composition:

| Ingredient | % by Weight | % by Weight Range |
|---|---|---|
| Beeswax | 20 | 6–26 |
| Mineral Oil | 69 | 40–80 |
| Osokerite | 5 | 1–10 |
| Paraffin Wax | 5 | 1–10 |
| Diol or Diol Ester[c] | 1 | 0.2–2.0 |
| Total | 100 | |

Another high quality protein containing cleansing cream has the following composition:

| Ingredient | % by Weight | % by Weight Range |
|---|---|---|
| Almond Oil | 30 | 10–50 |
| Beeswax | 10 | 5–17 |
| Lanolin | 10 | 5–15 |
| Spermaceti | 8 | 2–14 |
| Protein | 10 | 2–18 |
| Diol or Diol Ester[c] | 2 | 0.2–5.0 |
| Water | 30 | 10–40 |
| Total | 100 | |

For example, suitable face powder formulations prepared in accordance with the present technique may comprise the following formulations:

FACE POWDER FORMULATIONS

| Ingredients | % by Weight | | | Wt. % Range |
|---|---|---|---|---|
| | Light | Medium | Heavy | |
| Protein Powder | 10 | 10 | 10 | 2–30 |
| Zinc Oxide | 15 | 20 | 30 | 5–50 |
| Talc | 62 | 49 | 38 | 10–70 |
| Zinc Stearate | 5 | 5 | 4 | 1–7 |
| Kaolin | 5 | 10 | 10 | 1–15 |
| Titanium Dioxide | | 3 | 5 | 1–10 |
| Diol or Diol Ester[c] | 2 | 2 | 2 | 0.2–5.0 |
| Perfume | 1 | 1 | 1 | 0.5–2.0 |
| Total | 100 | 100 | 100 | |

The additives of the present invention are particularly desirable when used in conjunction with cosmetics and personal care compositions which contain protein as one ingredient.

What is claimed is:

1. A method of inhibiting the growth of public health implicated bacteria, yeasts and molds in cosmetic and personal care preparations containing edible oils and organic nitrogen compounds comprising incorporating in the preparations an effective amount of a linear aliphatic 1,3-diol having 5 to 15 carbon atoms in the molecule, whereby the preparation is preserved against deterioration.

2. The method of claim 1 wherein the linear aliphatic 1,3-diol is present at about 0.05 to 5.0% by weight based on the total weight of the preparation.

3. The method of claim 1 wherein the linear aliphatic 1,3-diol is present at from about 0.1 to 2.0% by weight based on the total weight of the preparation.

4. The method of claim 1 wherein the diol has from 7 to 10 carbon atoms in the molecule.

5. A method of preserving cosmetic and personal care compositions containing edible oils and proteins in a nondeteriorated state comprising adding to the composition from about 0.5% to about 5% by weight based on the total weight of composition of linear aliphatic 1,3-diols having 5 to 15 carbon atoms.

* * * * *